United States Patent [19]

Lawrenz et al.

[11] Patent Number: 4,643,032
[45] Date of Patent: Feb. 17, 1987

[54] FRANGIBLE MOLTEN METAL SAMPLING DEVICE

[75] Inventors: Dennis A. Lawrenz, Bridgman; Ken A. Rinkenberg, Stevensville, both of Mich.

[73] Assignee: Leco Corporation, St. Joseph, Mich.

[21] Appl. No.: 729,170

[22] Filed: Apr. 30, 1985

[51] Int. Cl.⁴ .............................................. G01N 1/12
[52] U.S. Cl. .................................................. 73/864.53
[58] Field of Search ................... 73/864.52, 864.53; 65/153, DIG. 8, DIG. 9

[56] References Cited

U.S. PATENT DOCUMENTS

| | | |
|---|---|---|
| 1,145,837 | 7/1915 | Hoff .................................. 65/153 X |
| 2,139,114 | 12/1938 | Demers . |
| 2,143,982 | 1/1939 | Hare et al. . |
| 2,485,492 | 10/1949 | Hubbard et al. ................. 73/864.53 |
| 2,861,450 | 11/1958 | Ransley . |
| 2,970,350 | 2/1961 | Feichtinger . |
| 3,315,529 | 4/1967 | Feichtinger . |
| 3,369,406 | 2/1968 | Lowdermilk et al. . |
| 3,390,568 | 7/1968 | Taylor . |
| 3,452,602 | 7/1969 | Hackett . |
| 3,457,790 | 7/1969 | Hackett . |
| 3,501,963 | 3/1970 | Collins ............................. 73/864.53 |
| 3,534,614 | 10/1970 | Creswell ............................ 73/425.6 |
| 3,915,014 | 10/1975 | Judge et al. . |
| 3,967,505 | 7/1976 | Feichtinger . |
| 4,007,641 | 2/1977 | Kelsey . |
| 4,170,139 | 10/1979 | Narita et al. . |
| 4,428,245 | 1/1984 | Nakamura et al. ............. 73/864.52 |
| 4,445,390 | 5/1984 | Atwell .............................. 73/864.52 |
| 4,535,640 | 8/1985 | Falk ................................... 73/864.55 |
| 4,537,747 | 8/1985 | Castaneda .......................... 422/100 |

FOREIGN PATENT DOCUMENTS

| | | |
|---|---|---|
| 1922677 | 11/1970 | Fed. Rep. of Germany . |
| 2035420 | 1/1972 | Fed. Rep. of Germany . |
| 39-8648 | 5/1964 | Japan . |
| 53-2358 | 3/1972 | Japan . |
| 1460024 | 8/1973 | United Kingdom . |
| 2040750A | 11/1979 | United Kingdom . |
| 623130 | 2/1977 | U.S.S.R. . |

Primary Examiner—Jerry W. Myracle
Attorney, Agent, or Firm—Price, Heneveld, Cooper, DeWitt & Litton

[57] ABSTRACT

A sampling device for obtaining samples from a molten metal bath includes a pair of concentric tubes spaced from one another and coupled at at least one end by a frangible interconnection such that the inner tube can be readily removed once the sample is taken and the frangible connection broken.

11 Claims, 6 Drawing Figures

U.S. Patent  Feb. 17, 1987  4,643,032
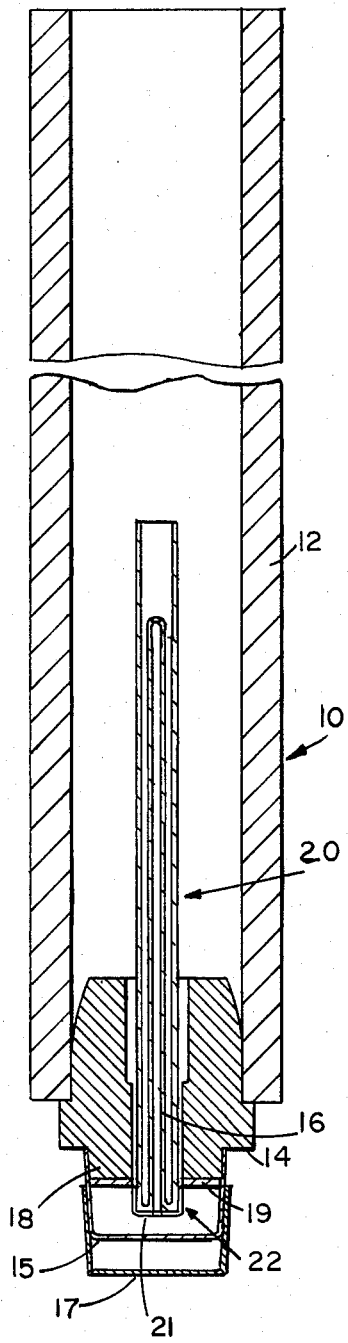
FIG. 1
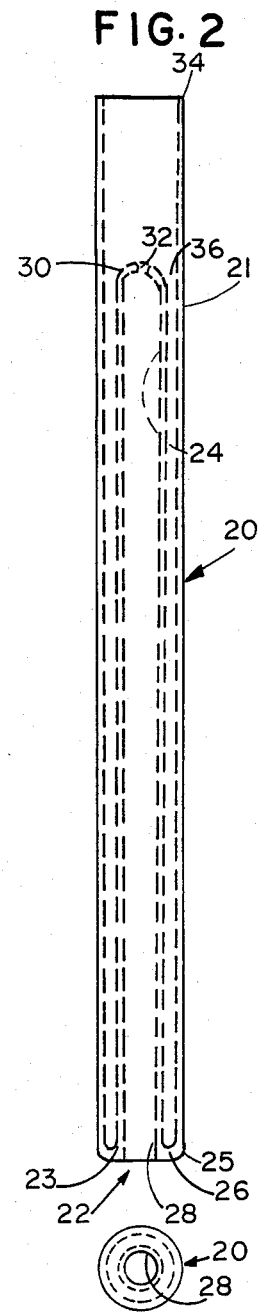
FIG. 2
FIG. 3
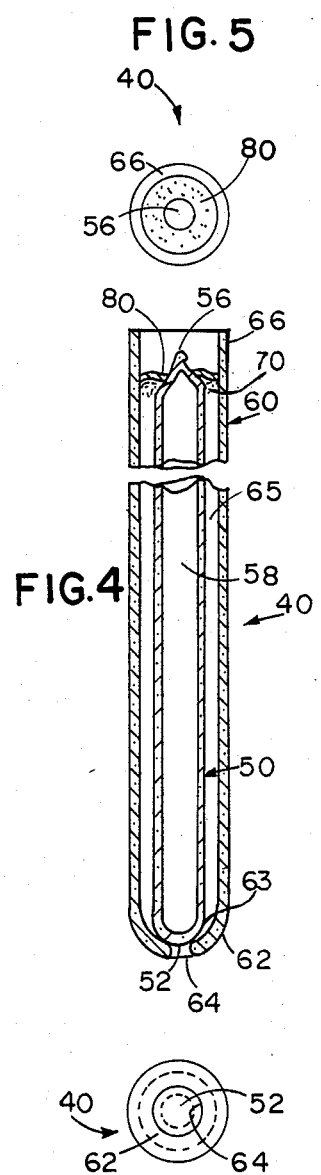
FIG. 5
FIG. 4
FIG. 6

FRANGIBLE MOLTEN METAL SAMPLING DEVICE

BACKGROUND OF THE INVENTION

The present invention pertains to an immersible molten metal sampling device and particularly to one which includes a frangible element for removing the sample holding portion of the device.

There exists a variety of molten metal sampling devices which are immersed in a molten metal bath for example in a steel manufacturing process such that a sample of the melt can be taken to determine the contents of the melt during the steel manufacturing process. U.S. Pat. No. 4,445,390 discloses a sampling device for the removal of a sample from a molten metal bath to capture the total hydrogen content of a sample. In this and other metallic evacuated tube samplers however, the molten metal bonds to the metallic wall surfaces of the sampler and when the solid sample is analyzed therefor the resulting pin-shaped sample includes not only the molten metal desired to be analyzed but also a portion of the sampling device itself.

Glass tube samplers have been employed in the past and typically constitute a single evacuated glass tube which is immersed into the molten bath and subsequently removed and chilled in first a water bath and subsequently in liquid nitrogen in order to prevent the escape of hydrogen from the sample. Inasmuch as it is necessary to relatively rapidly chill the sample to prevent the escape of hydrogen it is necessary to quickly remove the sampling device from the sample holding tube. In the past this has been very difficult inasmuch as typically the tube is encapsulated in a ceramic material which is part of a holder as shown for example in U.S. Pat. No. 3,369,406. Naturally the longer it takes to remove the sampling device from the holder for chilling, the more free hydrogen can escape and the accuracy of the resulting analysis of the sample is adversely affected.

SUMMARY OF THE PRESENT INVENTION

The sampling device of the present invention overcomes the difficulties of the prior art sampling devices including the difficulties in rapidly handling the sample defining chamber to provide for processing of the sample as quickly as possible The sampling device of the present invention achieves these goals by providing a sample receiving chamber and a support member for supporting the sample receiving chamber with respect to a sample holder which is immersed into the molten metal bath. A frangible coupling couples the sample receiving chamber and the support member such that once a sample has been taken, the frangible coupling member can be broken and the sample receiving chamber with the solidifying sample contained therein quickly removed from the support which is immersed into the molten metal bath. Thus the sampling device of the present invention provides a sample receiving chamber which is readily stripped from the sample holding apparatus for removal to either a chilling process or to a chamber such as described in copending U.S. patent application Ser. No. 676,782 entitled SAMPLING CELL AND METHOD filed on Nov. 30, 1984 and assigned to the present assignee.

In one embodiment of the present invention the sample receiving chamber is open ended such that a hydrostatic sample is taken. In another embodiment of the present invention the sample defining chamber is an evacuated chamber In either embodiments, the sample defining or receiving chamber is preferably formed of an inner tube which is frangibly coupled to an outer concentric tube in turn held by the sample holding apparatus immersed into the molten metal bath. The frangible connection permits the inner sample receiving tube to be quickly stripped from the apparatus for handling of the sampling with minimal loss of hydrogen or other gas from the device.

These and other features, objects and advantages of the present invention will become apparent upon reading the following description thereof together with reference to the accompanying drawings in which:

BRIEF DESCRIPTION OF THE DRAWINGS

FIG. 1 is a vertical cross-sectional view of a molten metal sampling device of the present invention shown mounted in a sample holding apparatus for immersion into a molten metal bath;

FIG. 2 is an enlarged side elevational view of the sampling device shown in FIG. 1;

FIG. 3 is a bottom plan view of the sampling device shown in FIG. 2;

FIG. 4 is an enlarged fragmentary cross-sectional view of an alternative embodiment of the sampling device of the present invention;

FIG. 5 is a top plan view of the structure shown in FIG. 4: and

FIG. 6 is a bottom plan view of the structure shown in FIG. 4.

DETAILED DESCRIPTION OF THE PREFERRED EMBODIMENT

Referring initially to FIG. 1 there is shown a sampling device holder 10 which is used for supporting the molten metal sampling device 20 in position as it is immersed into a molten metal bath. In the embodiment shown device 10 is employed for taking molten metal samples from a furnace or ladle which typically includes a layer of slag on the surface. The device 10 includes an elongated cylindrical fiberboard tube 12 into which there is fitted a sample device holder element 14 comprising a plug molded of a sand and resin material which is force fitted into the lower end of tube 12. Element 14 includes a cylindrical central bore 16 which mechanically holds the generally cylindrical sampling device 20 in position with a sample receiving end 22 projecting outwardly from the holder 14 and protected by a pair of spaced steel end caps 15 and 17 which provide protection for the end 22 of sampling device 20 as the tube is immersed through the layer of slag. The steel caps 15 and 17 are press fit over an annular shoulder 18 of holder 14 and a steel chill washer 19 covers the exposed lower annular surface of shoulder 18 to prevent the molten metal from eroding element 14 while it is immersed. The cylindrical sampling device 20 is secured within element 14 to project outwardly into the space between washer 19 and the inner surface of cap 15 a distance in the preferred embodiment of approximately ½ of an inch. An aluminum foil cap 21 optionally is placed over the projecting cylindrical end 22 of sampling device 20 to prevent entry of foreign material into the sampling device 20 during handling and storage prior to assembly into the holder 10 and also provides some killing ability for the molten metal sample. For use in sampling molten material in ingots for example where there typically is no slag layer, end caps 15 and 17 are not employed. The sampling device 10 is of generally conventional construction and the sample device 20 held to holder 14 in a conventional manner by, for example, cementing the interface between the outer cylindrical portion of sampling device 20 and the bore 16 of holder 14 with a ceramic cement or hot glue. The sampling device 20 is inserted into element 14 prior to its fitting into the lower end of cardboard tube 12. Having described the overall construction of the holder for sampling device 20, the sampling device 20 is now described in detail in conjunction with the enlarged views of FIGS. 2 and 3.

Device 20 comprises a pair of concentric cylindrical tubes including an outer tube 21 and an inner tube 24 integrally joined at their first respective ends 23 and 25 by an integral frangible section 26. The lower end 22 of device 20 therefore provides an open cylindrical end 28 for the admission of molten metal material into the inner cylindrical bore of inner tube 24. The second end 30 of tube 24 opposite open end 28 is restricted and defines a circular venting aperture 32 which allows the venting of gases from the tube as it is hydrostatically filled from end 22 by molten metal. Inner tube 24 is substantially shorter than outer tube 21 such that the second end 30 of tube 24 is positioned within the second open end 34 of tube 24 as illustrated in FIG. 3. The inner diameter of tube 21 is somewhat greater than the outer diameter of tube 24 such that a cylindrical space 36 extends between the tubes.

In the embodiment of the invention shown in FIGS. 1-3, sampling device 20 is manufactured of two separate quartz tubes with the outer tube 21 having a length of 7 inches and comprising an 11 millimeter o.d. tube. Inner tube 24 has a length of 6 inches and comprises an 8 millimeter o.d. tube. The wall thickness of each of the tubes 21 and 24 is approximately 1 millimeter thereby providing a ½ millimeter cylindrical gap 36 between the tubes. Inner tube 21 is first restricted to define the circular aperture 32 which has a diameter of approximately 0.08 inches and subsequently the tubes are held in concentric relationship and fused to define the frangible connection 26 at their lower ends. By employing quartz tubes, the fusing step defines the fusable coupling means between the first and second tubes. Device 20 is formed as described above using conventional glass forming techniques.

In use, once the sample holder 10 shown in FIG. 1 is immersed and the sampling device 20 fills hydrostatically, the tube is removed from the molten metal bath and the projecting end 22 is broken typically by mechanically rapping the lower end of the sample holder 10 against a hard surface or alternately by utilizing pliers to snap off the end. This breaks the frangible connection 26 between the inner and outer tubes allowing the inner tube 24 to slide out from the supporting outer tube 21. A rod shaped sample is thereby formed and held within inner tube 24 and can be quickly immersed in the chilling process first in water and subsequently liquid nitrogen for subsequent analysis. Alternatively, the pin can be introduced into the sampling cell disclosed in the above identified copending patent application. By providing the frangible connection between the outer support tube 21 and the inner sampling tube 24, therefore the inner tube can be quickly and easily removed in a minimum amount of time thereby greatly reducing the amount of hydrogen which can escape from the cooling pin sample during the sample removing and handling process.

An alternative embodiment of the present invention is shown in FIGS. 4–6 in which again a dual wall sampling tube structure is employed. In the embodiment of the sampling device 40 shown in FIG. 6, an evacuated inner tube 50 is positioned within a generally cylindrical outer tube 60. Tube 60 has a first end 62 which is narrowed to define a circular opening 64 having a diameter less than the outer diameter of tube 50. The opposite or second end 66 of tube 60 is of the same diameter as the tube. Tube 50 comprises a cylindrical tube having a first end 52 which is closed in a thinner wall section than the tube itself while the second opposite end 56 of tube 50 is sealed off while a vacuum is drawn on the tube thus evacuating the tube to subatmospheric pressure. This is done by a conventional glass blowing process. Tube 50 is then held in concentric relationship within tube 60 with end 52 in abutment against the inner annular shoulder 63 surrounding aperture 64 while a commercially available ceramic fiber packing material 70 is placed around end 56 of tube 50 and in the annular space 65 between the tubes to support the free end 56 of the tube in concentric relationship with end 66 of the outer tube. Subsequently a thin layer of ceramic cement 80 such as Sauereisen cement is applied to the outer annular surface of the ceramic fiber material 70 to hold the fiber material in place. The combination of the fibrous material and ceramic cement 80 define a frangible interconnection of tubes 50 and 60 at ends 56 and 66. As with sampling device 20 shown in FIGS. 1-3, the inner sample defining chamber 50 of the device shown in FIGS. 4–6 can be readily removed once a sample is taken since a cylindrical air space 65 extends between tubes 50 and 60.

Sampling device 40 is inserted in the holder 10 in the same manner as sampling device 20 and the relatively thin end 52 of the quartz inner tube 50 melts upon immersion in the molten metal bath allowing the evacuated tube to draw molten metal material into its inner pin sample defining cavity 58. The interface between end 52 of tube 50 and shoulder 63 is sufficiently tight to prevent molten metal from entering the cylindrical space 65 which also is prevented by the utilization of the ceramic packing material 70 and cement 80 from the open end 66 of tube 60.

In the preferred embodiment of the tube shown in FIGS. 4–6, outer tube 60 was an 11 millimeter outer diameter quartz tube while tube 50 was an 8 millimeter outer diameter quartz tube each tube having a wall thickness of approximately 1 millimeter and a length of about 6 inches. Tube sampling device 40 like sampling device 20 is broken near the tip end 62 for removal of the inner tube 50. During the breaking process the frangible connection at the opposite end also breaks such that tube 50 can be readily removed from the broken lower end of tube 60 for handling of the pin sample contained therein. The thickness of end 52 of tube 50 is about 0.0015 inches and is formed by a conventional glass blowing technique. Tube 50 is evacuated to a pressure of approximately 100 microns during its manufacturing to provide the evacuated mold defining chamber.

In both embodiments shown, an outer tube is provided which is held by the sample immersion holder device 10 and an inner tube space coaxially from the outer tube and is coupled to the outer tube in a frangible manner such that it can be quickly and easily removed upon the taking of a molten metal sample. Although in the preferred embodiment the tubes are made of quartz, it would be possible to make the tubes of other suitable material as long as a frangible interconnection was provided such that the inner tube could be quickly and readily removed from the outer tube by fracturing the frangible interconnections. These and other modifications to the preferred embodiments of the invention will become apparent to those skilled in the art but will fall within the spirit of scope of the invention as defined in the appended claims.

The embodiments of the invention in which an exclusive property or privilege is claimed are defined as follows.

1. A device for use in the sampling of molten metal comprising:
    a cylindrical tube of vitreous material having an outer cylindrical section with first and second ends and an inner cylindrical section having first and second ends, said inner and outer sections integrally joined only at said first ends with said inner section coaxially aligned with and radially spaced from said outer section, said inner section having a smaller outer diameter than the inner diameter of said outer section to provide a cylindrical space between said sections, and wherein said second end of said inner section is restricted to define a generally circular opening having a diameter less than the inner diameter of said inner section.

2. The apparatus as defined in claim 1 wherein said inner section is shorter in length than said outer section such that said second end of said inner section is Positioned within said outer section.

3. A device for use in the sampling of molten metal comprising:
    a cylindrical tube of vitreous material having an outer cylindrical section with first and second ends and an inner cylindrical section having first and second ends, wherein said second end of said inner section is restricted to define a generally circular opening having a diameter less than the inner diameter of said inner section, said inner and outer sections integrally joined at said first ends with said inner section coaxially aligned with and radially spaced from said outer section, said inner section having a smaller outer diameter than the inner diameter of said outer section to provide a cylindrical space between said sections, and wherein said inner section is shorter in length than said outer section such that said second end of said inner section is positioned within said outer section.

4. The apparatus as defined in claim 3 wherein said vitreous material is quartz.

5. A device for use in the sampling of molten metal comprising:
    a cylindrical tube of vitreous material having an outer cylindrical section with first and second ends and an inner cylindrical section having first and second ends, wherein said second end of said inner section is restricted to define a generally circular opening having a diameter less than the inner diameter of said inner section, said inner and outer sections integrally joined at said first ends with said inner section coaxially aligned with and radially spaced from said outer section, and wherein said inner section has a smaller outer diameter than the inner diameter of said outer section to provide a cylindrical space between said sections.

6. A frangible device for use in the sampling of molten metal comprising:
    a cylindrical sample tube defining a sample receiving chamber, wherein said sample tube is evacuated;
    a support member comprising a cylindrical support tube having a diameter such that said sample tube can be fitted coaxially within said support tube for supporting said sample tube; and
    frangible coupling means comprising a ceramic material including a ceramic fiber and a ceramic cement coating said fiber for holding said fiber in place and coupled adjacent ends of said sample and support tubes for coupling said sample tube to said cylindrical support tube such that said sample tube can be rapidly removed from said cylindrical support tube for processing of a sample contained therein by breaking said frangible coupling means.

7. A frangible device for use in the sampling of molten metal comprising:
    means defining a sample receiving chamber;
    a support member for supporting said means defining a sample receiving chamber;
    frangible coupling means for coupling said means defining a sample receiving chamber to said support member such that said means defining a sample receiving chamber can be rapidly removed from said support member for processing of a sample contained therein by breaking said frangible coupling means; and
    wherein said means defining a sample receiving chamber is evacuated.

8. A device for use in obtaining samples from a molten metal bath comprising:
    an outer cylindrical tube having one end with inwardly deflected wall means defining a reduced diameter opening;
    an inner cylindrical tube having an outer diameter less than the inner diameter of said outer tube and greater than said reduced diameter opening, said inner tube having one end positioned adjacent to and supported by said wall means; and
    frangible coupling means coupling said inner and outer tubes in concentric relationship to one another at a location remote from said one end of said inner tube such that said inner tube can be readily removed from said outer tube upon breaking of said frangible coupling means.

9. The apparatus as defined in claim 8 wherein said outer and inner tubes are made of quartz.

10. The apparatus as defined in claim 9 wherein said frangible coupling means joins one end of each of said tubes.

11. A device for use in obtaining samples from a molten metal bath comprising:
    an outer cylindrical tube;
    an inner cylindrical tube having an outer diameter less than the inner diameter of said outer tube wherein said inner tube is a sealed evacuated tube; and
    frangible coupling means coupling said inner and outer tubes in concentric relationship to one another such that said inner tube can be readily removed from said outer tube upon breaking of said frangible coupling means.

* * * * *